(12) United States Patent
Ervin et al.

(10) Patent No.: US 10,006,879 B2
(45) Date of Patent: Jun. 26, 2018

(54) SITE SPECIFIC CHEMICALLY MODIFIED NANOPORE DEVICES

(75) Inventors: Eric N. Ervin, Park City, UT (US); John J. Watkins, West Jordan, UT (US); Geoffrey A. Barrall, San Diego, CA (US)

(73) Assignee: ELECTRONIC BIOSCIENCES, INC., San Diego, CA (US)

( * ) Notice: Subject to any disclaimer, the term of this patent is extended or adjusted under 35 U.S.C. 154(b) by 960 days.

(21) Appl. No.: 14/110,089

(22) PCT Filed: Apr. 11, 2012

(86) PCT No.: PCT/US2012/033142
§ 371 (c)(1),
(2), (4) Date: Dec. 30, 2013

(87) PCT Pub. No.: WO2012/142174
PCT Pub. Date: Oct. 18, 2012

(65) Prior Publication Data
US 2014/0106472 A1      Apr. 17, 2014

Related U.S. Application Data

(60) Provisional application No. 61/474,690, filed on Apr. 12, 2011.

(51) Int. Cl.
| | |
|---|---|
| *G01N 27/327* | (2006.01) |
| *G01N 33/543* | (2006.01) |
| *G01N 33/551* | (2006.01) |
| *G01N 33/487* | (2006.01) |
| *B82Y 15/00* | (2011.01) |

(52) U.S. Cl.
CPC ... *G01N 27/3278* (2013.01); *G01N 33/48721* (2013.01); *G01N 33/54386* (2013.01); *G01N 33/54393* (2013.01); *G01N 33/551* (2013.01); *B82Y 15/00* (2013.01)

(58) Field of Classification Search
None
See application file for complete search history.

(56) References Cited

U.S. PATENT DOCUMENTS

| | | | |
|---|---|---|---|
| 5,530,101 | A | 6/1996 | Queen et al. |
| 5,707,622 | A | 1/1998 | Fong et al. |
| 5,990,296 | A | 11/1999 | Pastan et al. |
| 5,994,524 | A | 11/1999 | Matsushima et al. |

(Continued)

FOREIGN PATENT DOCUMENTS

| | | |
|---|---|---|
| WO | WO 2006/130299 | 12/2006 |
| WO | WO 2008/060324 | 5/2008 |
| WO | WO 2012/142174 | 10/2012 |

OTHER PUBLICATIONS

Office Action dated Jan. 30, 2017 in U.S. Appl. No. 14/408,936, filed on Dec. 17, 2014 and published as U.S. 2015-0204873 on Jul. 23, 2015.

(Continued)

*Primary Examiner* — Rebecca L Martinez
(74) *Attorney, Agent, or Firm* — Grant IP, Inc.

(57) ABSTRACT

Provided are site specific chemically modified nanopore devices and methods for manufacturing and using them. Site specific chemically modified nanopore devices can be used for analyte sensing and analysis, for example.

20 Claims, 4 Drawing Sheets

(56) References Cited

U.S. PATENT DOCUMENTS

| | | | |
|---|---|---|---|
| 6,099,842 | A | 8/2000 | Pastan et al. |
| 6,245,894 | B1 | 6/2001 | Matsushima et al. |
| 6,342,221 | B1 | 1/2002 | Thorpe et al. |
| 6,395,557 | B1 | 5/2002 | Fouillet et al. |
| 7,777,505 | B2 | 8/2010 | White et al. |
| 2002/0012843 | A1 | 1/2002 | Fowlkes et al. |
| 2002/0182627 | A1 | 12/2002 | Wang et al. |
| 2003/0146091 | A1 | 8/2003 | Vogel et al. |
| 2004/0120861 | A1 | 6/2004 | Petroff |
| 2005/0074778 | A1 | 4/2005 | Letant et al. |
| 2007/0116610 | A1 | 5/2007 | Cuppoletti |
| 2008/0121534 | A1* | 5/2008 | White .................. B01D 67/006 205/787.5 |
| 2009/0258372 | A1 | 10/2009 | Lopez et al. |
| 2011/0041978 | A1 | 2/2011 | Wallace |
| 2011/0121840 | A1 | 5/2011 | Sanghera et al. |
| 2011/0130312 | A1 | 6/2011 | Notte et al. |
| 2012/0190040 | A1 | 7/2012 | Talebpour |
| 2012/0222958 | A1 | 9/2012 | Pourmand |
| 2012/0255862 | A1 | 10/2012 | Dunnam et al. |
| 2014/0174927 | A1 | 6/2014 | Bashir |
| 2015/0204873 | A1 | 7/2015 | Ervin et al. |
| 2017/0276678 | A1 | 9/2017 | Ervin et al. |

OTHER PUBLICATIONS

Ali et al., "Biosensing and supramolecular bioconjugation in single conical polymer nanochannels. Facile incorporation of biorecognition elements into nanoconfined geometries" Journal of the American Chemical Society (2008) 130(48):16351-16357.

Ali et al., "Metal ion affinity-based biomolecular recognition and conjugation inside synthetic polymer nanopores modified with iron-terpyridine complexes" Journal of the American Chemical Society (2011) 133(43):17307-17314.

Sexton et al., "Developing synthetic conical nanopores for biosensing applications" Molecular Biosystems (2007) 3(10):667-685.

Siwy et al., "Protein biosensors based on biofunctionalized conical gold nanotubes" Journal of the American Chemical Society (2005) 127(14):5000-5001.

Extended European Search Report dated Dec. 12, 2014 in EP Application No. 12770608.3, filed on Apr. 11, 2012 and published as EP 2 697 394 on Feb. 19, 2014.

Kohler and Milstein, "Continuous cultures of fused cells secreting antibody of predefined specificity" Nature (1975) 256:495-497.

Movileanu et al., "Detecting protein analytes that modulate transmembrane movement of a polymer chain within a single protein pore" Nature Biotechnology (2000) 18:1091-1095.

St Groth and Scheidegger, "Production of monoclonal antibodies: strategy and tactics" J. Immunol. Methods (1980) 5:1-21.

Sun and Mirkin, "Scanning Electrochemical Microscopy with Slightly Recessed Nanotips" Anal. Chem. (2007) 79(15):5809-5816.

International Search Report and Written Opinion dated Jul. 2, 2012 in International Application No. PCT/US2012/33142, filed on Apr. 11, 2012 and published as WO 2012/142174 on Oct. 18, 2012.

International Preliminary Report on Patentability dated Oct. 24, 2013 in International Application No. PCT/US2012/33142, filed on Apr. 11, 2012 and published as WO 2012/142174 on Oct. 18, 2012.

Vlassiouk et al., Journal of the American Chemical Society (2009) 131(23):8211-8220.

International Search Report and Written Opinion dated Nov. 1, 2013 in International Application No. PCT/US2013/046318, filed on Jun. 18, 2013 and published as WO 2013/192178 on Dec. 27, 2013.

International Preliminary Report on Patentability dated Dec. 23, 2014 in International Application No. PCT/US2013/046318, filed on Jun. 18, 2013 and published as WO 2013/192178 on Dec. 27, 2013.

Supplementary European Search Report dated Jan. 13, 2016 in European Patent Application No. EP 13807736.7, filed on Jun. 18, 2013 and published as EP 2 861 998 on Apr. 22, 2015.

Office Action dated Aug. 23, 2016 in U.S. Appl. No. 14/408,936, filed Dec. 17, 2014 and published as U.S. 2015-0204873 on Jul. 23, 2015.

* cited by examiner

SITE SPECIFIC CHEMICALLY MODIFIED NANOPORE DEVICES

RELATED PATENT APPLICATION(S)

This patent application is a national stage application of international patent application no. PCT/US2012/033142, filed on Apr. 11, 2012 entitled SITE SPECIFIC CHEMICALLY MODIFIED NANOPORE DEVICES, naming Eric N. Ervin et al. as inventors, which claims the benefit of U.S. application No. 61/474,690, filed on Apr. 12, 2011, entitled SITE SPECIFIC CHEMICALLY MODIFIED NANOPORE FOR PROTEIN, VIRUS, AND BIOMARKER DETECTION, naming Eric Ervin et al. as inventors. The entirety of the foregoing patent applications is incorporated herein by reference, including all text, tables and drawings.

FIELD

The technology relates in part to nanopore devices. Such devices are useful for sensing target molecules.

BACKGROUND

A nanopore can be utilized as an analyte sensor (e.g., resistive-pulse sensing method or stochastic sensing) by using a direct current (DC) potential across a membrane which includes a nanopore, and separates two electrolyte solutions. The DC potential can generate an ionic current flow through the nanopore, where the magnitude of the current being generated is determined by the: (i) geometry of the nanopore, (ii) internal charge characteristics of the nanopore, and (iii) conductivity of the electrolyte solution within the nanopore. When an analyte molecule contained in an electrolyte solution blocks or translocates through a nanopore, the conductance of the nanopore decreases, resulting in a decrease in the DC current response. The frequency of blocking/translocating events can be used to determine the analyte concentration, while the magnitude and duration of the blocking/translocating events can provide information about the identity of the analyte.

SUMMARY

Described herein are site specific chemically modified nanopore (SS-CMN) devices, and methods of manufacturing and using them. In an aspect, provided are nanopore devices that include: a solid support that includes a first surface, an opposing second surface, and a wall or walls between the first surface and the second surface; a channel in the solid support that includes a proximal opening at the first surface, a distal opening at the second surface and an interior sidewall surface; and a non-cyclic analyte binding molecule attached effectively by covalent linkage to the interior sidewall surface of the channel, which analyte binding molecule can specifically bind to an analyte; whereby the analyte binding molecule forms a sensing region in the channel.

In another aspect, provided are methods for detecting the presence, absence, amount or property of an analyte, which methods include: (a) contacting a sample that may include an analyte with a nanopore device under conditions in which the analyte, if present in the sample, is captured in a sensing region of the device, which nanopore device includes: a solid support that includes a first surface, an opposing second surface, and a wall or walls between the first surface and the second surface; a channel in the solid support that includes a proximal opening at the first surface, a distal opening at the second surface and an interior sidewall surface; and non-cyclic analyte binding molecules attached effectively by covalent linkage to the interior sidewall surface of the channel, each of which analyte binding molecules can specifically bind to an analyte; whereby the analyte binding molecules form the sensing region in the channel; and (b) measuring a property of the sensing region, whereby the presence, absence, amount or property of the analyte in the sample is determined by a change in the property measured in (b).

Also provided in another aspect are methods for manufacturing nanopore devices, which methods include: (a) modifying at least a portion of an interior sidewall surface of a channel of a solid support with a first set of modifying molecules, which solid support includes a first surface, an opposing second surface, and a wall or walls between the first surface and the second surface, and which channel includes a proximal opening at the first surface, a distal opening at the second surface and the interior sidewall surface; (b) conjugating non-cyclic analyte binding molecules to the first set of modifying molecules, which analyte binding molecules can specifically bind to an analyte; whereby a nanopore device is fabricated. In methods for manufacturing SS-CMN devices described herein, second, third, fourth and fifth modifying molecules are optional, and can be used in any combination (e.g., first and fourth molecules but not second, third or fifth molecules, and variants thereof).

In some embodiments, there are no cyclic molecules linked or effectively linked to any portion of a nanopore device. In certain embodiments, there are no cyclic molecules linked or effectively linked to an inner surface of a channel within a nanopore device.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

DETAILED DESCRIPTION

Alpha hemolysin (alpha-HL), a transmembrane protein, frequently is used as a nanopore in sensing experiments.

Sensing experiments often are performed by inserting an alpha-HL channel into a synthetic planar lipid bilayer (PLB), suspended over the orifice of a synthetic support, followed by measuring the conductance of the channel. Nanopore sensing elements utilizing protein channels have been shown to detect a variety of analytes, non-limiting examples of which include: metal ions, DNA segments, proteins of various sizes, organic molecules, and the like. Synthetic PLB's which contain an alpha-HL channel sometimes are fragile, which has limited the ability to make practical sensing devices. Additionally, many currently used ion channel systems cannot be dehydrated or easily shipped. Site specific chemically modified nanopore (SS-CMN) device embodiments described herein offer excellent pore size reproducibility, stability, and also offer the added benefit of being able to be chemically or biologically engineered.

Synthetic nanopores often are produced in silicon films by ion/electron beam irradiation, or synthetic polymer membranes fabricated using the track-etched method. These nanopores, which can be cylindrical or conical in nature, have been used to detect DNA, various proteins, and nanoparticles. Reproducibility in pore size and geometry, especially in pores sizes below 10 nm, limit the ability to create a practical chemical sensing device. For nanopores to be successful as chemical sensors, each nanopore must interact with the analyte molecule in an identical and reproducible fashion. Since the ionic current difference produced from one analyte to another analyte can be on the order of a few pico-amps (pA), the current differences resulting from variation in pore size must be below this value in order to allow for direct comparison between sensors.

Nanopores also have been recently used for proteomic analysis. Proteomics is the study of proteins, more specifically the study of protein structure, function, and concentration in a given sample. Current methods of determining both the presence and concentration of a protein in a given sample include enzyme linked immunosorbent assay (ELISA), surface plasmon resonance (SPR), and mass spectrometry (MS). Nanopore methods for determining both the presence and concentration of a protein offer many advantages over ELISA, SPR, and MS, and non-limiting examples of the advantageous benefits of the use of nanopore methods include:
1. expensive equipment is not required,
2. expensive reagents are not required in large quantities,
3. the analysis can work at the single molecule level allowing for the ability to differentiate between the molecule of interest and other molecules or contaminants in a system,
4. the readout can be continuous, meaning the platform is never filled up and the molecule of interest is not consumed,
5. arrays can be produced allowing for multiple target molecules to be analyzed on a single platform, and
6. the nanopore typically does not need experienced personnel to run the sensing experiment.

Site Specific Chemically Modified Nanopore (SS-CMN) Devices

Site specific chemically modified nanopore (SS-CMN) devices are well suited for use as nanopore sensors for a variety of biological or chemical based target molecules, non-limiting examples of which include protein, virus, organic contaminants, chemical contaminants, biomarkers, DNA, RNA, other small molecules, the like and combinations thereof. A SS-CMN device often is chemically modified such that it contains an analyte specific binding or "sensing" region in a channel. SS-CMN devices include a highly-stable synthetic nanopore, fabricated from a robust, low capacitance material, the production of which can result in near uniform sensing region sizes. The sensing region size can be determined by the original pore diameter alone or along with the tether length used to attach the binding molecule to the surface of the pore, as described in greater detail hereafter, for example. SS-CMN devices described herein provide several advantageous benefits when compared to currently existing nanopore sensor technology, as shown in the table below.

|  | Reproducible Size | Adequate Noise Performance | Stable/robust Platform | High Voltage Tolerance | Ability to localize functionality |
|---|---|---|---|---|---|
| αHL in a PLB | Yes | Yes - 1 pA at 10 kHz | No - PLBs are fragile | No - max is about 300-700 mV | Yes |
| Synthetic Pores | No - not below 10 nm | No - due to high capacitance and dielectric loss | Yes | Yes | No |
| SS-CMN | Yes | Yes | Yes | Yes | Yes |

Functionality of a SS-CMN device often is determined by an analyte binding molecule in effective connection with a zone below the proximal opening of a channel in the device. An analyte binding molecule can be any molecule that functions to bind, trap, or associate with a target analyte.

The solid support of a nanopore device can be manufactured from any suitable material. Non-limiting examples of materials suitable for use in a solid support of a nanopore device include glass, Si, $SiO_2$, $Si_3N_4$, alumina, nitrides, diamond, quartz, sapphire metals, ceramics, polymers (e.g., Teflon, polycarbonate) the like or combinations thereof. Non-limiting examples of types of glass suitable for generating nanopore membrane systems include fused silica glass, ninety-six percent silica glass, soda-lime silica glass, borosilicate glass, aluminosilicate glass, lead glass, doped glass comprising desired additives, functionalized glass comprising desired reactive groups, the like and combinations thereof. Non-limiting examples of minerals (e.g., quartz) suitable for generating nanopore membrane systems include quartz, tridymite, cristobalite, coesite, lechatelierite, stishovite and combinations thereof. In certain embodiments, a solid support may comprised a hydrophobic material, such as Teflon, or it may be modified in a manner that renders one or more surfaces of the solid support (e.g., channel interior, channel exterior) hydrophobic (e.g. mildly hydrophobic, substantially hydrophobic).

Solid support thickness can range from about 100 nanometers (nm) to 5 millimeters (mm) in thickness (e.g., about 100 nm, about 150 nm, about 200 nm, about 250 nm, about 300 nm, about 350 nm, about 400 nm, about 500 nm, about 600 nm, about 700 nm, about 800 nm, about 900 nm, about 1000 nm (e.g., about 1 μm), about 2 μm, about 3 μm, about 4 µm, about 5 µm, about 6 µm, about 7 µm, about 8 µm, about 9 µm, about 10 µm, about 15 µm, about 20 µm, about 25 µm, about 30 µm, about 35 µm, about 40 µm, about 45 µm, about 50 µm, about 60 µm, about 70 µm, about 80 µm, about 90 µm, 100 µm, about 110 µm, about 120 µm, about 130 µm, about 140 µm, about 150 µm, about 175 µm, about 200 µm, about 225 µm, about 250 µm, about 300 µm, about 350 µm, about 400 µm, about 450 µm, about 500 µm, about 600 µm, about 700 µm, about 800 µm, about 900 µm, 1000 µm (e.g. 1 mm), about 2 mm, about 3 mm, about, about 4 mm, or about 5 mm).

The channel in a solid support of a SS-CMN device often is chemically modified and dimensioned to form a sensing region. The minimum radius of the channel often ranges from about 0.10 nanometers to about 50 µm (e.g., about 0.10 nanometers, about 0.15 nanometers, about 0.20 nanometers, about 0.25 nanometers, about 0.5 nanometers, about 1 nanometer, about 1.5 nanometers, about 2 nanometers, about 2.5 nanometers, about 3 nanometers, about 3.5 nanometers, about 4 nanometers, about 4.5 nanometers, about 5 nanometers, about 6 nanometers, about 7 nanometers, about 8 nanometers, about 9 nanometers, about 10 nanometers, about 15 nanometers, about 20 nanometers, about 25 nanometers, about 30 nanometers, about 35 nanometers, about 40 nanometers, about 45 nanometers, about 50 nanometers, about 60 nanometers, about 70 nanometers, about 80 nanometers, about 90 nanometers, about 100 nanometers, about 125 nanometers, about 150 nanometers, about 175 nanometers, about 200 nanometers, about 250 nanometers, about 300 nanometers, about 350 nanometers, about 350 nanometers, about 400 nanometers, about 500 nanometers, about 600 nanometers, about 700 nanometers, about 800 nanometers, about 900 nanometers, about 1000 nanometers (e.g., 1 µm), about 1.5 µm, about 2 µm, about 2.5 µm, about 3 µm, about 3.5 µm, about 4 µm, about 5 µm, about 10 µm, about 15 µm, about 20 µm, about 25 µm, about 30 µm, about 35 µm, about 40 µm, about 45 µm, or about 50 µm). The channel formed in the solid support is of any suitable geometry, and sometimes has a substantially circular, oval, square, rectangular, rhomboid, parallelogram, or other like cross-section. The channel formed in the solid support is of any suitable side profile, and sometimes has a substantially cylindrical, conical, frustrum (e.g., tapering or expanding conical; conical frustrum) profile. A SS-CMN device often is composed of a single frustrum- or conical-shaped channel embedded in a suitable material. Channels can be formed as known in the art and as described herein.

In SS-CMN devices provided herein, analyte binding molecules often are effectively linked to an interior sidewall surface of the channel between the first surface and second surface of the device. An effectively linked analyte binding molecule sometimes is directly linked or indirectly linked (e.g., effectively linked by one or more tethers or modifying molecules)) to an interior surface of the channel. Analyte binding molecules often are not effectively linked to a portion of the solid support or device other than on an interior surface of the channel (e.g., not effectively linked to the first surface, second surface, and/or exterior of the device). Portions of the device that are not effectively linked to an analyte binding molecule may be uncoated or may be coated with one or more modifying molecules that do not link to an analyte binding molecule (also referred to as "blocking molecules"). In some embodiments, a first set of blocking molecules coats a surface (e.g., first surface and device exterior surfaces) and a second set of blocking molecules coats another surface (e.g., a portion of the interior surface of the channel not in the zone to which tethers and/or analyte binding molecules are linked). In some embodiments, the first set and the second set of blocking molecules are the same or different. In certain embodiments the entire channel and second surface of the device are coated with analyte binding molecules.

Analyte binding molecules often are effectively linked to a portion of the interior surface of the channel between the first surface and second surface. This portion of the interior surface is referred to as a "zone" herein. The zone often extends from a first depth from the proximal opening of the channel to a second depth from the proximal opening of the channel. The first depth sometimes is co-extensive with the first surface or may be a certain distance from the first surface of the device. The second depth sometimes is closer to the distal opening of the channel than the first depth. In certain embodiments, the first depth is co-extensive with the first surface and the second depth is co-extensive with the second surface. The distance between the first depth and the second depth sometimes is about 0.1 nm to about 5 millimeters, and the distance between the first surface of the device and the first depth sometimes is about 0 millimeters to about 5 millimeters. The zone to which the analyte binding molecules are effectively linked often extends around the circumference of the interior surface of the channel.

The analyte binding molecules and optional tethers to which they can be linked can effectively fill a portion of the channel and thereby define a void within the channel. This void may be of any suitable shape for a sensing region in the channel to which one or more analyte molecules can bind at a particular time.

The void sometimes is substantially circular, and sometimes the void is concentric with the proximal opening of the channel. The effective center point of the void may be substantially concentric with the center point of the proximal opening, and the two center points often are in different cross sectional planes of the channel. In some embodiments, the void is not concentric with the proximal opening of the channel. The effective radius of the void sometimes is about 1 to 100 times the effective radius of an analyte that specifically binds to one or more of the analyte binding molecules that define the void. The effective radius of the void sometimes is about 1 to 2 times the effective radius of an analyte that specifically binds to one or more of the analyte binding molecules that define the void. The effective radius of the void sometimes is determined by the equation $Radius_{sensing} = Radius_{channel} - (Length_{tether} + Length_{analyte\ binding\ molecule})$, as addressed herein. In some embodiments, the minimum effective radius of the sensing region, or void, in the channel is about 0.10 nanometers to about 500 nanometers and sometimes about 0.25 nanometers to about 500 nanometers (e.g., about 0.10 nanometers, 0.15 nanometers, 0.20 nanometers, 0.25 nanometers, 0.3 nanometers, 0.4 nanometers, 0.5 nanometers, 0.75 nanometers, about 1.0 nanometers, about 2.0 nanometers, about 3.0 nanometers, about 4.0 nanometers, about 5.0 nanometers, about 10.0 nanometers, about 15 nanometers, about 20 nanometers, about 25 nanometers, about 30 nanometers, about 35 nanometers, about 40 nanometers, about 50 nanometers, about 60 nanometers, about 70 nanometers, about 80 nanometers, about 90 nanometers, about 100 nanometers, about 120 nanometers, about 140 nanometers, about 160 nanometers, about 180 nanometers, about 200 nanometers, about 220 nanometers, about 240 nanometers, about 260 nanometers, about 280 nanometers, about 300 nanometers, about 400 nanometers, or about 500 nanometers).

The analyte and analyte binding molecule that specifically binds to the analyte sometimes are referred to herein as members of a "binding pair." Non-limiting examples of a binding pair member include an antibody, antibody fragment, antibody receptor, hapten, anti-hapten, protein, polypeptide, peptide, nucleic acid (e.g., double-stranded DNA (dsDNA), single-stranded DNA (ssDNA), or RNA), a nucleotide, a nucleotide analog or derivative (e.g., bromodeoxyuridine (BrdU)), an alkyl moiety (e.g., methyl moiety on methylated DNA or methylated histone), an alkanoyl moiety (e.g., an acetyl group of an acetylated protein (e.g., an acetylated histone)), an alkanoic acid or alkanoate moiety (e.g., a fatty acid), a glyceryl moiety (e.g., a lipid), a phosphoryl moiety, a glycosyl moiety, an ubiquitin moiety, lectin, aptamer, receptor, ligand, metal ion, and the like, and a binding pair may be any combination of the foregoing. A binding pair member may be part of, or all of, one of the following non-limiting examples: a pathogen (e.g., bacterium (e.g., anthrax), virus), biomarker, chemical contaminant, organic contaminant, drug (e.g., elicit drug (e.g., cocaine)), toxin (e.g., anthrax toxin, ricin) or combination thereof. Non-limiting examples of binding pairs include antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, nucleic acid/complementary nucleic acid (e.g., DNA, RNA, PNA), and chemical reactive group/complementary chemical reactive group (e.g., sulfhydryl/maleimide, sulfhydryl/haloacetyl derivative, amine/isotriocyanate, amine/succinimidyl ester, and amine/sulfonyl halides).

An analyte sometimes comprises all of a portion of a protein, polypeptide or peptide. An analyte sometimes is a sub-region of a protein, such as in the N-terminus, C-terminus, extracellular region, intracellular region, transmembrane region, active site (e.g., nucleotide binding region or a substrate binding region), a domain (e.g., an SH2 or SH3 domain) or a post-translationally modified region (e.g., phosphorylated, glycosylated or ubiquinated region), for example. The analyte sometimes is the modification moiety or a portion thereof (e.g., the glycosyl group or a portion thereof) or is the modification moiety in conjunction with amino acids of the protein or peptide to which it is linked (e.g., a phosphoryl group in combination with one or more amino acids of the protein or peptide).

An analyte binding molecule sometimes is an antibody or antibody fragment. Antibodies sometimes are IgG, IgM, IgA, IgE, or an isotype thereof (e.g., IgG1, IgG2a, IgG2b or IgG3), sometimes are polyclonal or monoclonal, and sometimes are chimeric, humanized or bispecific versions of such antibodies. Polyclonal and monoclonal antibodies that bind specific antigens are commercially available, and methods for generating such antibodies are known. In general, polyclonal antibodies are produced by injecting an isolated antigen into a suitable animal (e.g., a goat or rabbit); collecting blood and/or other tissues from the animal containing antibodies specific for the antigen and purifying the antibody. Methods for generating monoclonal antibodies, in general, include injecting an animal with an isolated antigen (e.g., often a mouse or a rat); isolating splenocytes from the animal; fusing the splenocytes with myeloma cells to form hybridomas; isolating the hybridomas and selecting hybridomas that produce monoclonal antibodies which specifically bind the antigen (e.g., Kohler & Milstein, Nature 256:495 497 (1975) and StGroth & Scheidegger, J Immunol Methods 5:1 21 (1980)). Examples of monoclonal antibodies are anti MDM 2 antibodies, anti-p53 antibodies (pAB421, DO 1, and an antibody that binds phosphorylser15), anti-dsDNA antibodies and anti-BrdU antibodies, are described hereafter.

Methods for generating chimeric and humanized antibodies also are known (see, e.g., U.S. Pat. No. 5,530,101 (Queen, et al.), U.S. Pat. No. 5,707,622 (Fung, et al.) and U.S. Pat. Nos. 5,994,524 and 6,245,894 (Matsushima, et al.)), which generally involve transplanting an antibody variable region from one species (e.g., mouse) into an antibody constant domain of another species (e.g., human). Antigen-binding regions of antibodies (e.g., Fab regions) include a light chain and a heavy chain, and the variable region is composed of regions from the light chain and the heavy chain. Given that the variable region of an antibody is formed from six complementarity-determining regions (CDRs) in the heavy and light chain variable regions, one or more CDRs from one antibody can be substituted (i.e., grafted) with a CDR of another antibody to generate chimeric antibodies. Also, humanized antibodies are generated by introducing amino acid substitutions that render the resulting antibody less immunogenic when administered to humans.

An antibody fragment utilized as an analyte binding molecule sometimes is a Fab, Fab', F(ab)'2, Dab, Fv or single-chain Fv (ScFv) fragment, and methods for generating antibody fragments are known (see, e.g., U.S. Pat. Nos. 6,099,842 and 5,990,296). In some embodiments, an analyte binding molecule is a single-chain antibody fragment, which can be constructed by joining a heavy chain variable region with a light chain variable region by a polypeptide linker (e.g., the linker is attached at the C-terminus or N-terminus of each chain) using recombinant molecular biology processes. Such fragments often exhibit specificities and affinities for an antigen similar to the original monoclonal antibodies. Bifunctional antibodies sometimes are constructed by engineering two different binding specificities into a single antibody chain and sometimes are constructed by joining two Fab' regions together, where each Fab' region is from a different antibody (e.g., U.S. Pat. No. 6,342,221). Antibody fragments often comprise engineered regions such as CDR-grafted or humanized fragments. In certain embodiments the binding partner is an intact immunoglobulin, and in other embodiments the binding partner is a Fab monomer or a Fab dimer. For fragments or antibodies comprising a portion or all of a Fc region, a sensing region in a device may include one or more tethers linked to an amino acid or other portion of the Fc region.

Analyte binding molecules effectively linked to a zone in the channel sometimes are homogeneous or heterogeneous. Where the analyte binding molecules are heterogeneous, two or more different types of analyte binding molecules may be effectively linked to a particular zone (e.g., 2, 3, 4, 5, 6, 7, 8, 9, 10 or more analyte binding molecules may be effectively linked to a particular zone). Different analyte binding molecules may be linked to a zone by the same types of tethers or different types of tethers.

An analyte binding molecule often specifically binds to an analyte. The term "specifically binds" refers to an analyte binding molecule binding to an analyte in preference to binding other molecules in a particular assay in which a device described herein is utilized. A specific binding interaction discriminates over non-specific binding interactions by about 2-fold or more, often about 10-fold or more, and sometimes about 100-fold or more, 1000-fold or more, 10,000-fold or more, 100,000-fold or more, or 1,000,000-fold or more. An analyte often binds to an analyte binding molecule by reversible binding (e.g., non-covalent binding), and sometimes by non-reversible binding (e.g., covalent binding).

The effective linkage or attachment of an analyte binding molecule to a solid support surface occurs via a chemical attachment, in certain embodiments. Analyte binding molecules sometimes are directly attached to the channel of the solid support without intermediate molecules. Analyte binding molecules often are effectively or indirectly attached to the channel of the solid support via one or more intermediate molecules. The intermediate molecules sometimes are referred to herein as "tethers" or "modifying molecules." A modifying molecule can effectively link an analyte binding molecule to a solid support channel surface in some embodiments. In certain embodiments, a modifying molecule can coat a surface (e.g., surface of the device not in the channel and/or zone in the channel not linked to tethers or analyte binding molecules) and effectively block the linkage of analyte binding molecules ("blocking molecule"). Linkage between a tether and analyte binding molecules and/or solid support channel surface, and/or linkage between modifying molecules and solid support surface, sometimes is non-covalent, and often is covalent.

Any suitable modifying molecule, tether and/or chemical attachment can be utilized. A modifying molecule or tether sometimes is a linear or branch chain chemical compound having a length that can be chemically controlled and having ends that can link to the analyte binding molecule on one end and the channel of the solid support on the other (e.g., covalently link). A modifying molecule or tether may be of any suitable length, allowing for the option of altering the sensing region radius to approximately match that of the target molecule, in certain embodiments. A modifying molecule and tether generally comprise at least one chemically reactive moiety that permits linkage of the molecule to a surface of the device (e.g., zone on the inner wall of a channel). A tether often includes at least two chemically reactive moieties, one that permits linkage of the tether to a surface of the device (e.g., zone on the inner wall of a channel) and another that permits linkage of the tether to an analyte binding molecule. The chemically reactive moieties on a tether may be the same or different, and different reactive moieties may react with the same or different chemistry. The chemically reactive moieties generally are capable of effecting chemical attachments, which attachments may be covalent or non-covalent. Non-limiting examples of chemical attachments suitable for use for effectively connecting a binding molecule to a solid support include: silanes, thiols, phosphonic acid, polyethylene glycol (PEG), the like and combinations thereof. In certain embodiments involving SS-CMN devices fabricated from glass, silane often is chosen as a tether molecule.

In some embodiments, a chemical attachment is chosen from a group of silanes of the appropriate length. Silanes generally bind to a glass surface via a silicon-oxygen covalent bond. In some embodiments, silane attachments provide a mechanism for covalently attaching the binding molecule. A silane may include one or more chemical substituents other than hydrogen, in some embodiments, including, but not limited to alkyl, alkoxy, cyano, carboxy, ester, amino and the like. In certain embodiments, a silane has a structure according to Formula I:

Formula I or a salt or isomer thereof, where:
each $R^1$, $R^2$ and $R^3$ independently is hydrogen, —OH, C1-C20 alkyl, substituted C1-C20 alkyl, C1-C20 alkoxy, substituted C1-C20 alkoxy, —C(O)—C1-C20 alkyl (alkanoyl), substituted —C(O)—C1-C20 alkyl, —C(O)—C6-C10 aryl (aroyl), substituted —C(O)—C6-C10 aryl, —C(O)OH (carboxyl), —C(O)O—C1-C20 alkyl (alkoxycarbonyl), substituted —C(O)O—C1-C20 alkyl, —$NR^aR^b$, —C(O)$NR^aR^b$ (carbamoyl), substituted C(O)$NR^aR^b$, halo, nitro, or cyano,
the substituents on the alkyl, aryl or heterocyclic groups are hydroxy, C1-C10 alkyl, hydroxyl C1-C10 alkylene, C1-C6 alkoxy, C3-C6 cycloalkyl, C1-C6 alkoxy C1-C6 alkylene, amino, cyano, halogen or aryl;
each $R^a$ and $R^b$ independently is hydrogen, C1-C6 alkyl, C3-C8 cycloalkyl, C1-C6 alkoxy, halo C1-C6 alkyl, C3-C8 cycloalkyl C1-C6 alkyl, C1-C6 alkanoyl, hydroxy C1-C6 alkyl, aryl, aryl C1-C6 alkyl, Het, Het C1-C6 alkyl, or C1-C6 alkoxycarbonyl; and
X is a leaving group (e.g., hydroxyl, halogen (e.g., bromine, chlorine, fluorine, iodine)). In certain embodiments a silane is 3-cyanopropyldimethylchlorosilane.

A tether can provide a mechanism for covalently attaching an analyte binding molecule, and also can effectively decrease the channel size in the solid support. In certain embodiments, silane attachments allow the effective radius of a SS-CMN device sensing region to substantially match that of the target analyte. The outer diameter or effective length of a tether molecule sometimes is about 0.1 nanometer to about 20 nanometers (e.g., about 0.2, 0.3, 0.4, 0.5, 0.6, 0.7, 0.8, 0.9, 1.0, 1.5, 2, 3, 4, 5, 6, 7, 8, 9, 10 or 15 nanometers). Matching the opening diameter of the pore to the target molecule can prevent significant ion current flow around the target molecule once the target molecule is captured, in some embodiments.

Methods of attaching a chemical tether (e.g. silanes) to a binding molecule and/or a channel, which can be referred to as "crosslinking," can occur between a reactive group at the end of the tether and a complementary reactive group on (i) on the outside of the binding molecule, and/or (ii) channel solid support. This attachment, which results in the covalent attachment of the binding molecule (e.g. direct or indirect attachment to the solid support), can be an irreversible or reversible covalent attachment. Methods of forming the covalent attachment of the binding molecule at the orifice of the solid support include, but are not limited to, an amine reacting with a N-Hydroxysuccinimide (NHS) ester, an imidoester, a pentafluorophenyl (PFP) ester, a hydroxymethyl phosphine, an oxiran or any other carbonyl compound; a carboxyl reacting with a carbodiimide; a sulfhydryl reacting with a maleimide, a haloacetyl, a pyridyldisulfide, and/or a vinyl sulfone; an aldehyde reacting with a hydrazine; any non-selective group reacting with diazirine and/or aryl azide; a hydroxyl reacting with isocyanate; a hydroxylamine reacting with a carbonyl compound; the like and combinations thereof. In some embodiments a secondary crosslinking molecule can be used to link a tether or other modifying molecule to an analyte binding molecule.

In some embodiments, the actual minimum channel radius can be made larger with the same fabrication steps described herein, from about 0.25 nm to about 1,000 nm, for example. The area that is modified near the proximal opening of the channel with the attachment linkers or tethers for the binding molecules can be made longer, about 2 nm to about 5,000,000 nm in length, for example. In the latter embodiments analyte molecules, (for example, antibodies or chemical analyte species) can be bound for a time at the sensing region. The concentration of these antibodies or other analyte molecules can be determined via a current rectification measurement instead of analyzing a single binding event. A rectification measurement can constitute an averaged measurement looking at a few to many molecules bound to the sensing region at the same time. Ion current rectification, defined as an increase in ion conduction at a given polarity and a decrease in ion conduction for the same voltage magnitude at the opposite polarity, occurs in conical shaped pores due to the voltage dependent solution conductivity within the aperture. The level of current rectification is due to the size of the sensing region, the surface charge, and the Debye length. By coating a device zone with an antibody via a tether a certain level of rectification can be measured, as the antibody binds to the antigen, or other analyte molecules in the sensing region, the current rectification of the pore is altered. The rectification change depends on the overall size and charge of the antigen or analyte molecule being bound. The rate of rectification change can be used to determine the concentration of the antigen or other analyte molecule in solution. In such embodiments a model is generated that directly relates the rate of current rectification change to the concentration of the species being detected.

Figure 1:
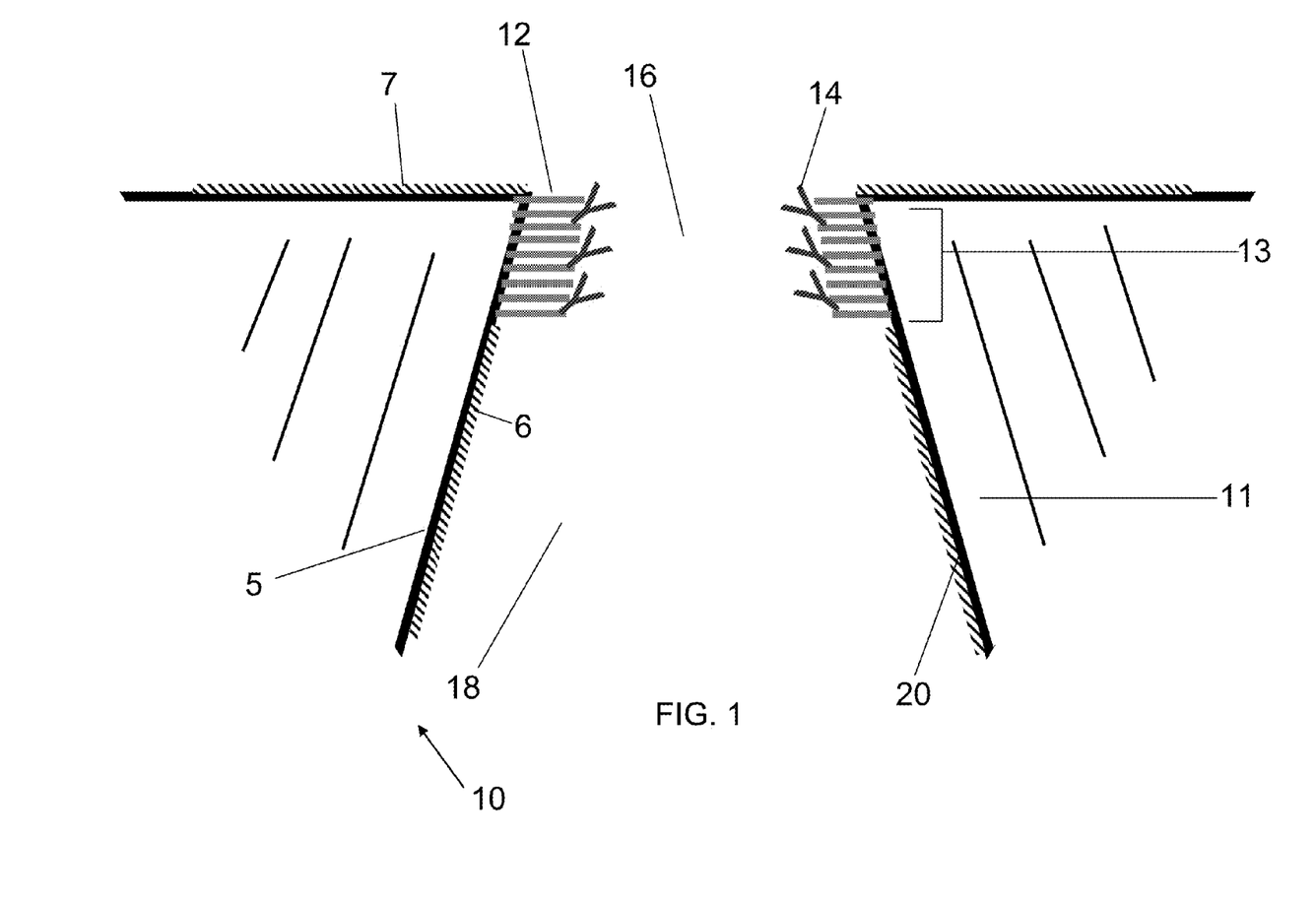
FIG. 1 is a schematic illustration, in cross section, of one embodiment of a site specific chemically modified nanopore (SS-CMN) device. The SS-CMN device depicted in the illustration includes a plurality of analyte binding molecules covalently attached to the pore aperture proximal portion of a conical glass nano-dimension pore.
Figure 2A:
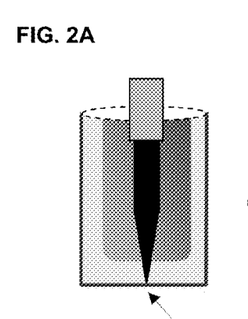
FIG. 2A to FIG. 2G illustrate a method used to fabricate a SS-CMN device. The method is further described herein.
Figure 2B:
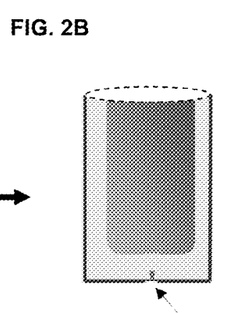
Figure 2C:
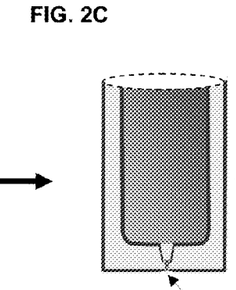
Figure 2D:
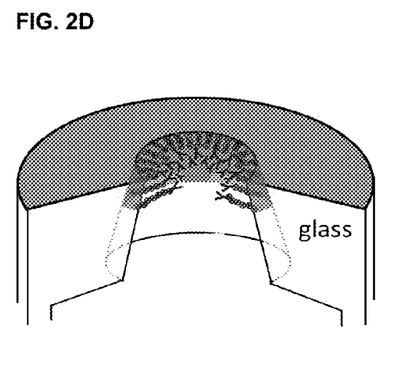
Figure 2E:
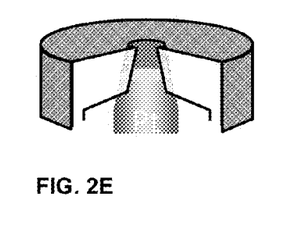
Figure 2F:
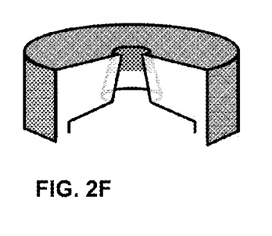
Figure 2G:
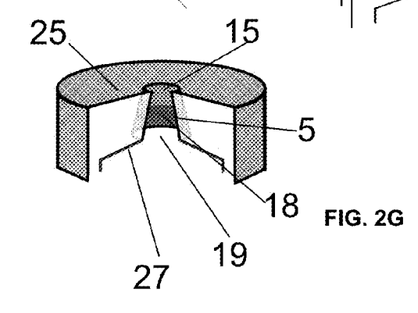

Specific embodiments of a SS-CMN device are shown in FIG. 1 and FIG. 2G herein. Device 10, depicted in FIG. 1, is generated by covalently attaching an analyte binding molecule 14 (e.g., an antibody in this embodiment) to the surface of a channel 18 penetrating a thin solid support membrane 11. The channel is of any suitable profile and is conical, frustrum (e.g., conical frustrum) or cylindrical in some embodiments. Membrane 11 can consist of any highly resistive material, including but not limited to glass, quartz, diamond, sapphire, silicon oxide, silicon nitride, aluminum oxide (alumina), Teflon, polycarbonate, graphene or other polymer film. Analyte binding molecule 14 is attached to membrane 11 by an effective covalent linkage via adapter molecule or tether 12. In FIG. 1, the analyte binding molecule 14 is covalently attached to tether molecule 12, and tether molecule 12 is covalently attached to a surface of channel 18. In certain embodiments, analyte binding molecule 14 can be attached to membrane 11 without an adapter molecule or tether 12. The effective void formed by binding molecules 14 attached to membrane 11, by tether molecule 12 is sensing region 16. Also illustrated in FIG. 1 is zone 13, at or below proximal opening 15 (shown in FIG. 2G), to which the binding molecules are covalently bound via tether molecules 12. In addition to proximal opening 15, also shown in FIG. 2G are channel 18, distal opening 19, first surface 25, second surface 27, and channel inner surface 5. FIG. 1 shows optional coatings 6 and 7 that define, in part, zone 13. Coatings 6 and 7 (i) may be the same or different, (ii) independently may be present or not present on a device, and/or (iii) may block linkage of an analyte binding molecule to surfaces to which the coatings are applied.

Fabrication of a SS-CMN Device

Fabrication of a SS-CMN can include the following general steps.

1. Fabrication of a Nanopore in a Synthetic Membrane

In some embodiments, the pore is conical in nature, although other geometries are also acceptable.

2. The First Surface of the Solid Support of the Nanopore Membrane Device can be Chemically Protected Leaving the Inside of the Pore Unmodified In certain embodiments, the first surface of the solid support is left uncoated. In certain embodiments, the first surface of the solid support is coated with a non reactive chemical group, such as a silane terminating in a cyano or methyl group, which helps prevent subsequent surface modifications, such as the functionalized tethers, from coating the first surface of the solid support. In certain embodiments, the nanopore is filled with a plug, such as metal, without requiring an additional step due to the fabrication of the device, such as a nanopore electrode. In certain embodiments, the nanopore is filled with a plug or is chemically protected prior to coating the first surface of the solid support in order to prevent the inside of the nanopore from being modified.

3. The Top of the Nanopore Plug is Removed

The plug (e.g., metal electrode, gel, chemical coating, polymer, the like and combinations thereof) is removed (e.g., electrochemically, chemically, mechanically, the like and combinations thereof), leaving the unmodified nanopore. In some embodiments, only the top portion of the plug is initially removed, allowing only a portion of the channel to be chemically modified.

4. The Diameter of the Synthetic Nanopore is Measured

The diameter of the synthetic nanopore can be measured by any appropriate means, including but not limited to electrochemical, microscopy methods, the like and combinations thereof.

5. An Appropriate Length Attachment Molecule is Chosen

The length of the attachment molecule (e.g., silane, thiol, the like and combinations thereof) can be chosen to generate nanopores of a predetermined size. Controlling pore size to substantially match the target molecule that will eventually be captured by a SS-CMN device can prevent significant ion current flow around the target molecule once it is captured. Pore size can be determined using the following formula:

$$\text{Radius}_{sensing\ region} = \text{Radius}_{channel} - (\text{Length}_{tether} + \text{Length}_{analytebindingmolecule}).$$

6. The Inside Aperture of the Synthetic Nanopore is Modified with the Attachment Molecule of Choice.

The inside of the pore can be modified by placing the membrane in a solution containing the chemical agent, in some embodiments. Sonication, pressure, temperature, the like and combinations thereof can be used to aid pore wetting.

7. The Rest of the Nanopore Plug is Removed

Any portion of the plug that was not removed in step 3, is removed as described in step 3.

8. The Rest of the Pore is Chemically Protected

The internal portion of the nanopore, below the sensing zone, and/or the other side of the membrane can be chemically protected, as described in step 2, to prevent nonspecific binding inside the membrane. This step along with step 2 helps restricts binding of the target molecule to the sensing zone of a SS-CMN device.

9. The Binding Molecule is Attached to Opening Aperture of the SS-CMN Device

The binding molecules are introduced into the synthetic membrane, in solution, and are allowed to bind to the orifice of the synthetic nanopore via the attachment molecules. The unbound binding molecules are then rinsed away leaving only binding molecules attached at the zone within the channel of the SS-CMN in place.

In some embodiments, a cross linking molecule that attaches to the attachment molecule on one end and the binding molecule on the other end may need to be introduced before introducing the binding molecule into the synthetic pore. This is necessary if the binding molecule does not have the chemistry needed to attach itself directly to the attachment molecule located on the surface of the channel, or if the analyte is relatively small.

In some embodiments the bulk of the nanopore plug or back of the plug can be removed first, leaving only a very small portion of the plug within the channel. Here, the entire surface of the channel could be modified with a protecting group. The very small remaining plug could then be removed and the internal aperture of the channel could be modified as detailed in steps 4 through 6.

In some embodiments a very small plug at the opening of the channel could be created. Here, the entire surface of the channel could be modified with a protecting group. The very small remaining plug could then be removed and the internal aperture of the channel could be modified as detailed in steps 4 through 6.

Although a SS-CMN device can be fabricated out of any suitable material, as described above, a detailed step-by-step method for fabricating an SS-CMN device starting with a glass nanopore electrode is described here.

While the fabrication of a nanopore electrode has previously been reported, the basic fabrication steps of the nanopore electrode followed by the steps to complete the SS-CMN device are described below:

1. A Pt wire is electrochemically etched in a NaCN solution to produce a sharp conical-shaped tip.
2. In certain embodiments, a smaller radius nanopore can be created when the sharpened Pt tip is etched a second time in a dilute $H_2SO_4$ solution, in order to produce an ultra sharp (with radii of curvature below 5 nm) Pt tip, free of an oxide layer.
3. The sharpened Pt wire is inserted into a glass capillary (quartz and sapphire capillaries may also be used).
4. The end of the capillary containing the sharpened Pt tip is flame sealed using either an $H_2$ flame, $H_2/O_2$ flame, laser, or other heating source.
5. The sealed glass bulb is polished down to the Pt wire, exposing a small Pt disk electrode.
6. The outside glass surface is modified, via silane chemistry. Typically, a silane that terminates in a CN functional group is used, but any silane that terminates in a hydrophobic group can be used. This silane is known for its non-reactive nature and ability to protect glass surfaces from nonspecific absorption. Silanizing the outer surface of the nanodisk electrode, prior to the like and combinations thereof the Pt nanodisk electrode, will prevent the cross linking silane that will be placed inside nanopore, from coating the outer surface.
7. The platinum (Pt) nanodisk electrode can be used to form a shallow, nanopore electrode. Here a known procedure can be used for removing a thin layer (less than or equal to 1 nm thick) of Pt (e.g., Sun, P. and Mirkin, M. V., Scanning Electrochemical Microscopy with Slightly Recessed Nanotips. Analytical Chemistry 2007, 79, (15), 5809-5816). Removing a thin layer of Pt can be accomplished by using a solution containing 60% (by volume) distilled water, 30% 5 M $CaCl_2$, and 10% HCl in combination with a 1.5 V amplitude, 2 MHz frequency AC waveform, applied for various amounts of time, to the shallow recessed Pt electrodes.

After the small shallow nanopore electrodes are fabricated, they can be converted into SS-CMN devices, as depicted in FIG. 2A to FIG. 2G. The SS-CMN devices generated as described herein often contain a ring of binding molecules bound to the aperture near the proximal opening of a nanopore. The bonds formed can be irreversible or reversible depending on the application. The inside of the shallow glass pore is silanized using a cross linker terminated silane (terminating in either $-NH_2$, $-ONH_2$, $-SH$, or other chemical crosslinking group). In some embodiments, the length of silane tether is pore diameter specific (e.g., the silane length is chosen so that the final pore diameter can approximately match that of the target molecule). This dense internal silane layer provides the mechanism for controlling the size of the nanopore, where necessary.

After the internal walls of the shallow support structure are silanized, the rest of the internal Pt is removed as described herein. The unmodified interior surface of the nanopore membrane often is chemically protected with a cyano silane, known for its non-reactive nature and ability to protect glass surfaces from nonspecific absorption. Treatment with a cyano silane helps prevent binding of the binding molecules in unwanted areas. In certain embodiments, other silanes or surface treatments may also be used or the surface may remain unmodified.

Once the site specific chemically modified nanopore membrane, (see FIG. 2C), is fabricated, binding molecules containing chemically reactive groups on their outer surface can be covalently attached to the inside of the chemically modified nanopore membrane, generating a SS-CMN device. In certain embodiments, the attachment occurs in solution, with the binding molecules being placed inside and outside of the chemically modified nanopore membrane. In some instances a crosslinking molecule which attaches to the attachment molecule on one end and the binding molecule on the other end may need to be introduced before introducing the binding molecule into the pore. This is necessary if the binding molecule does not have the chemistry needed to attach itself directly to the attachment molecule located on the surface of the nanopore. Once bound, the unbound binding molecules are rinsed away, leaving only binding molecules attached at the proximal opening aperture of the SS-CMN device in place.

A fabrication process embodiment of an SS-CMN device starting with a glass nanopore electrode is depicted in FIG. 2A to FIG. 2D. As shown in FIG. 2A, a linker, or tether, is covalently linked to a zone in the channel exposed after etching of the wire in the channel (e.g., a platinum wire). The tether is capable of linking to an analyte binding molecule. As shown in FIG. 2B, the wire is removed, which reveals another zone in the channel. As shown in FIG. 2C, the zone revealed by removal of the wire is coated with a modifying molecule that is not capable of linking to an analyte binding molecule and blocks attachment of analyte binding molecules. As shown in FIG. 2D, analyte binding molecules are linked to the tethers, often by a covalent linkage. FIG. 2E, FIG. 2F and FIG. 2G are enlarged views of areas in devices designed by each arrow in FIG. 2A, FIG. 2B and FIG. 2C, respectively, Applications Using SS-CMN Devices For many nanopore sensors, detection and/or differentiation occurs as the analyte molecule of interest interacts with or translocates through the nanopore orifice. In certain embodiments a SS-CMN device is used in an aqueous medium. Electrodes placed on both sides of the nanopore orifice are used to hold either a direct current (DC) voltage or an alternating current (AC) voltage, or AC/DC voltages across the sensing region, in some embodiments. Analyte detection and/or differentiation, is determined by monitoring and analyzing the fluctuations in the time varying current response between the two electrodes. The SS-CMN device can be used as a sensor element for numerous applications including, but not limited to the detection and discrimination of proteins, viruses, biomarkers, small solid particles, chemical agents chemical compounds, DNA, RNA the like and combinations thereof.

During use of a SS-CMN device, a conductive solution or electrolyte generally fills or is in contact with the interior and exterior of the SS-CMN device. Typically, the electrolyte is composed of ionic salts dissolved in a liquid. Ionic salts include but are not limited to sodium chloride (NaCl), potassium chloride (KCl), lithium chloride (LiCl), sodium bromide (NaBr), mixtures thereof, the like and combinations thereof. The liquid component of the electrolyte is typically water but may be any other suitable liquid in which the salt is soluble. The electrolyte may also be composed of an ionic liquid. Examples of ionic liquids include but are not limited to 1-Butyl-3-methylimidazolium hexafluorophosphate, 1-butyl-3,5-dimethylpyridinium bromide, the like and combinations thereof.

To measure the conductivity across a SS-CMN device, electrodes are placed on either side of the channel of the SS-CMN device. The electrodes are in contact with the conductive liquid on the interior and exterior sides. Non-limiting examples of suitable electrode materials include: silver, silver chloride, platinum, gold, carbon, the like and combinations thereof. An AC, DC or AC/DC voltage bias is applied across the two electrodes and the resulting current through the SS-CMN device is measured.

An advantageous benefit of SS-CMN devices described herein over other methods of detecting and differentiating between various analytes (e.g., proteins, viruses, the like and combinations thereof), is the ability of a SS-CMN device to detect analytes at the single molecule level. Designing a SS-CMN device having dimensions close to that of the target molecule ensures only one to a few target molecule binds at a time. Once bound, the target molecule can be released from the SS-CMN device spontaneously or with assisted release (e.g., reversed voltage polarity, reversed voltage polarity with increased magnitude, pressure flow). The robust nature, along with the general design of SS-CMN devices allow for both pressure drive and/or voltage drive release of the target molecule from its binding molecule counterpart.

In some embodiments, a SS-CMN device is fabricated using a conical or frustrum shaped nanopore, which focuses the electric field cross the nanopore at the opening orifice. By increasing the voltage being applied between the two electrode across the pore a large electrostatic driving force can be used to separate the target molecule from its binding molecule. Likewise, the ability to pressurize a SS-CMN device on one side can be used to separate the target molecule from its binding molecule. In this case a positive or negative pressure is applied to one side the SS-CMN device. This pressure can result in flow and a force being applied onto the target molecule aiding in its release from the binding molecule.

In certain embodiments, a SS-CMN device is used to study one or more kinetic parameters associated with a target molecule. Kinetic parameters can be considered properties of the sensing region, and properties of the analyte and analyte binding molecule in the sensing region. Non-limiting examples of kinetic parameters useful for detecting and/or determining the presence, absence, or concentration of a target molecule include: the on rate ($k_{on}$), the off rate ($k_{off}$), and affinity ($k_D = k_{off}/k_{on}$) of the target molecule/binding molecule interaction (e.g., antibody/antigen interaction). In the case of very strong target molecule/binding molecule interaction (e.g., small $k_{off}$ constants) voltage or pressure may be used to decrease the binding time (e.g. increase $k_{off}$). This could allow comparison of rate constants of two types of target molecules that have long lived binding times in a reasonable time frame.

In some embodiments, a SS-CMN device can be used to determine the presence, absence and concentration of a target molecule, even in the presence of an interfering molecule that has affinity for the binding molecule. Molecules with little or no affinity for the binding molecules in the pore, would simply translocate through the pore, resulting in very short current blocking event. The target molecule or the interfering molecule, which do bind to the pore would be captured and released numerous times (e.g. between about 2 and about 1000) and a statistical analysis of koff and/or the blocking levels can be carried out in order to verify the presence of the target molecule. In cases where the target molecule or interfering molecule bound very strongly to the pore (e.g. small koff) voltage and/or pressure could be used to increase koff or decrease the binding time, making rapid analysis of the presence and concentration of the target molecule possible.

Figure 3A:
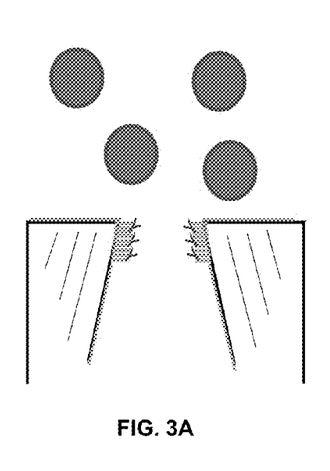
FIG. 3A to FIG. 3D is a schematic illustration of a SS-CMN device capturing a target analyte molecule (FIG. 3A and FIG. 3B). Also shown is the release of the captured target analyte molecule by the use of a force or voltage (FIG. 3C and FIG. 3D). Such methods of use are described in greater detail herein.
Figure 3B:
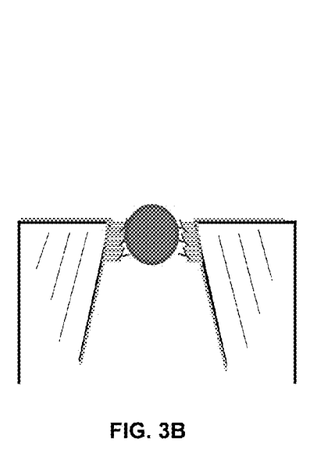
Figure 3C:
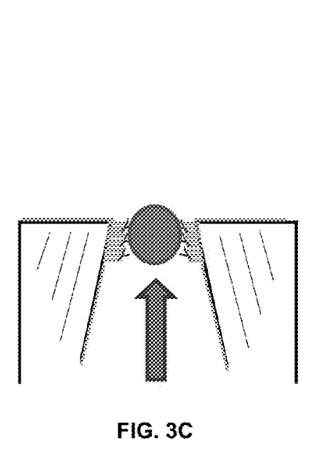
Figure 3D:
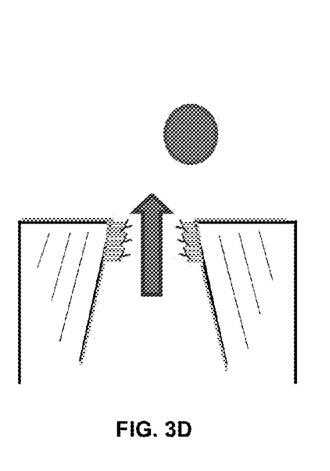

A schematic showing the use of voltage and/or pressure to increase koff is depicted in FIG. 3A to FIG. 3D. As shown in FIG. 3A, target analyte molecules are in solution and are free to interact with a sensing region in a nanopore device. As shown in FIG. 3B, one or a few target analyte molecules are captured by analyte binding molecules in the sensing region of the device. As shown in FIG. 3C, pressure or voltage is applied as a force on the captured analyte in the direction towards the proximal opening of the device. As shown in FIG. 3D, the force releases the target analyte from the device. The release of the target analyte resets the system for another analyte binding event and assessment of a property in the sensing region.

EXAMPLES

The examples set forth below illustrate certain embodiments and do not limit the technology.

Example 1: Preparation of a SS-CMN Device

This example describes the production of a SS-CMN device. In this example, a 25 µm diameter platinum (Pt) wire was electrochemically etched in a 6 M NaCN solution to produce a sharp conical-shaped tip. The etched Pt wire was then etched a second time in a dilute 0.1N $H_2SO_4$ solution to produce an ultra sharp Pt tip. The sharpened end of the electrochemically etched Pt wire was sealed to a depth of 25-100 µm into one end of a soda-lime glass capillary that was heated to softening using a $H_2$ flame. After cooling, the glass capillary was polished to expose a Pt nanodisk electrode, surrounded by a mirror finished glass membrane. This structure was achieved by polishing the glass on 1200 grit sandpaper and/or 0.05 µm alumina on a microcloth, wetted with ultrapure water. Disk exposure, and orifice radius, was monitored by measuring the limiting current of the Pt disk electrode in 5 mM ferrocene and 0.1 M $TBAPF_6$ in acetonitrile. The size of the Pt disk and resulting diameter of the proximal opening was approximately 100 nm.

The outside glass surface (first surface) of the nanopore device was chemically protected with cyano-silane (3-cyanopropyldimethylchlorosilane) modifying molecules, to limit non-specific binding. The nanopore device was rinsed with ultrapure water, ethanol, and acetonitrile prior to cyano-protection. The Pt disk electrode then was submerged in a 2% cyano-silane solution in acetonitrile for about 24 hr. Acetonitrile was stored over a 3 angstrom molecular sieve prior to use. After cyano-protection, the nanopore device was rinsed with acetonitrile, ethanol, and finally ultrapure water. The Pt wire of the cyano-protected electrode was then removed via electrochemical etching and mechanical removal. The Pt was etched using about 1.2 M $CaCl_2$ and a $20V_{PP}$ sine wave voltage at a frequency of 100 Hz. When the Pt wire was etched back about half the distance from the proximal opening to the distal opening, over a period of days to weeks, it was mechanically pulled from the glass.

Removing the entire Pt wire before further modification enabled generation of a sensing zone having a depth spanning from the first surface to the second surface. Once the Pt was removed, the interior surface of the channel was functionalized via silane chemistry, cross linker attachment, and finally antibody modification. First, the interior sidewall surface of the channel and the second surface of the nanopore device was silane-functionalized (tether) with 2% 3-aminopropyldimethylethoxysilane in acetonitrile. The channel was filled and submerged in this amino-silane solution for 24-72 hr. The amino-silane chemical modification provided active amino sites for reaction with a heterobifunctional crosslinker (sulfosuccinimidyl-4-[N-maleimidomethyl]cyclohexane-1-carboxylate, Sulfo-SMCC) (secondary crosslinking molecule). This crosslinker contains N-hydroxysuccinimide ester and maleimide groups to react with amine- and sulfhydryl groups, respectively. The channel of the nanopore device was reacted, or maleimide-activated, with a 2 mg/mL solution of Sulfo-SMCC in 0.15 M NaCl, 0.05-0.15 M sodium phosphate buffer (pH 7.2), and 10 mM EDTA. The maleimide-activation reaction was performed for 1 hr at room temperature, after which the device was rinsed with 0.15 M NaCl, 0.05-0.15 M sodium phosphate buffer (pH 7.2), and 10 mM EDTA and stored desiccated at 4 degrees Celsius until antibody attachment was performed (within 1-4 hr). Once the crosslinker reacted with the free amino groups of the silane coating, maleimide-activating the pore surface, a site for direct antibody attachment via a sulfhydryl was available.

An anti-cSNAP-25 antibody (analyte binding molecule) was provided as 1 mL of cell supernatant. The antibody was purified from the cell supernatant via a Pierce Antibody Clean-up Kit (Product #44600), and the purified antibody was then stored at 4 degrees Celsius for no longer than 1 week. Reactive sulfhydryl groups were introduced to the anti-cSNAP-25 monoclonal antibody by reducing the disulfide bonds in the hinge region via 2-mercaptoethylamine-HCl, producing free thiols to form stable thioether bonds with the maleimide groups of the crosslinker on the interior sidewall surface. The sulfhydryl groups were introduced by reacting 0.5 mL purified antibody with 0.5 M (prior to addition of antibody) 2-mercaptoethylamine-HCl in 0.15 M NaCl, 0.05-0.15 M sodium phosphate buffer (pH 7.2), and 10 mM EDTA. This reaction was performed at 37 degrees Celsius for 90 min. After the antibody had been reduced, it was purified via a polyacrylamide desalting column. Fractions that contained antibody were identified and collected via spectrophotometry absorbance at 280 nm. The reduced antibody was then reacted with the maleimide-activated surface of the interior sidewall surface. The nanopore device was filled with and submerged in the collected reduced antibody fractions for 4 hr at room temperature. The devices were then rinsed with 0.15 M NaCl, 0.05-0.15 M sodium phosphate buffer (pH 7.2), and 10 mM EDTA, and stored desiccated at room temperature. At this point, the SS-CMN device fabrication was complete.

In this Example 1, a particular effective radius of the channel was not intentionally selected by choosing particular tether and analyte binding molecules having particular lengths. As shown hereafter, antibody molecules formed a sensing region in the device useful for detecting analyte.

Example 2: Analyte Detection Using an SS-CMN Device

Figure 4:
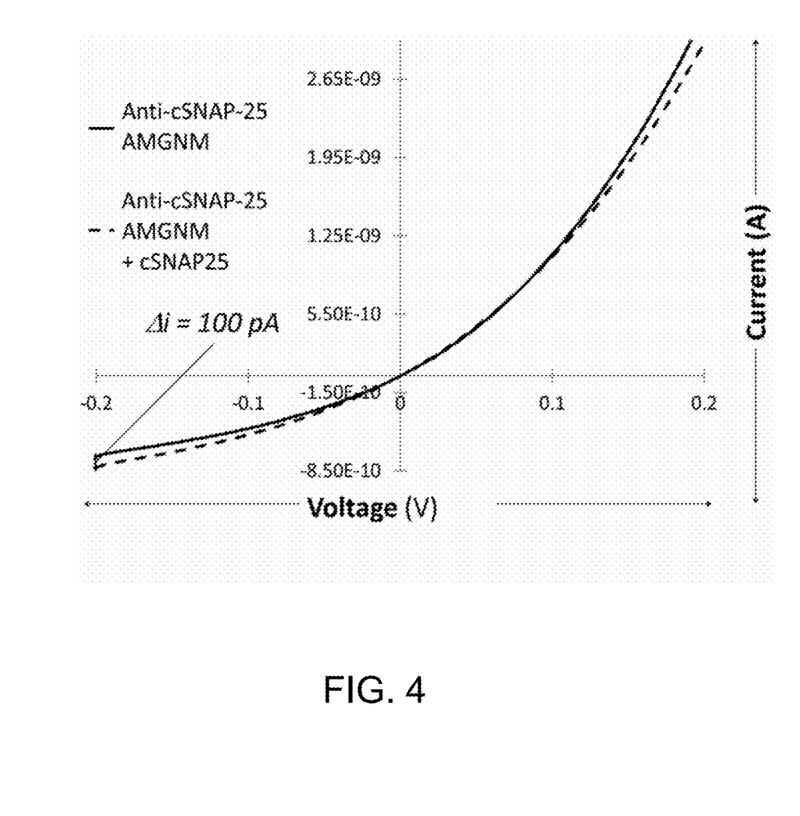
FIG. 4 shows a measured current response of a 100 nm diameter anti-cSNAP-25 coated SS-CMN before (solid line) and after (dashed line) exposure to cSNAP-25 (2 µM) as a function of the applied voltage (−200 to 200 mV).

The foregoing Example 1 demonstrates a method for producing a type of SS-CMN, and this Example 2 illustrates the use of the device to detect the presence of an analyte using a current rectification measurement. Described in this Example 2 is the detection of a cleaved SNARE protein known as SNAP-25 (analyte). The SS-CMN device coated with anti-cSNAP monoclonal antibodies (the analyte binding molecules) was used to detect free cSNAP-25 molecules (the analyte) in solution using a current rectification measurement. The device was prepared with one Ag/AgCl electrode in a bath of electrolyte (50 mM KCl, 10 mM HEPES, pH 7.2 with 10 mM EDTA) outside the proximal opening of the channel and one Ag/AgCl electrode in a bath of electrolyte (50 mM KCl, 10 mM HEPES, pH 5.3 with 10 mM EDTA) inside the capillary of the device outside the distal opening of the channel. The current through the channel as a function of voltage (from −200 to 200 mV) was recorded, as shown in FIG. 4 (solid line). The analyte cSNAP-25 then was added to the electrolyte bath outside the proximal opening of the channel at a concentration of 2 µM. The cSNAP-25 began immediately to bind to the antigen, which in turn began to neutralize the surface of the pore, resulting in a transition to a more ohmic response. The current through the channel as a function of voltage (from −200 mV to 200 mV) was recorded, as shown in FIG. 4 (dashed trace). The overall change in recitification at −200 mV was on the order of 100 pA between the two traces. This measurement can be repeated over time and the rate of current rectification change can be used to determine the concentration of the analyte. For example, the current rectification changes over time as more antibodies bind to the antigen. The rate of change can be used to determine concentration.

Example 3: Examples of Embodiments

Provided hereafter are non-limiting examples of certain embodiments of the technology described herein.

A1. A nanopore device, comprising:
a solid support that comprises a first surface, an opposing second surface, and a wall or walls between the first surface and the second surface;
a channel in the solid support that comprises a proximal opening at the first surface, a distal opening at the second surface and an interior sidewall surface; and
a non-cyclic analyte binding molecule attached effectively by covalent linkage to the interior sidewall surface of the channel, which analyte binding molecule can specifically bind to an analyte; whereby the analyte binding molecule forms a sensing region in the channel.

A2. The nanopore device of embodiment A1, wherein the device comprises a plurality of analyte binding molecules that are identical to one another.

A3. The nanopore device of embodiment A1, wherein the device comprises a plurality of analyte binding molecules that are a mixture of different analyte binding molecule species.

A4. The nanopore device of any one of embodiments A1 to A3, wherein the analyte binding molecule independently is chosen from an antibody, antigen, ligand, lectin, aptamer, receptor or combination thereof.

A5. The nanopore device of any one of embodiments A1 to A4, wherein the analyte binding molecule specifically binds to an analyte chosen from a peptide, polypeptide, antibody, antigen, or molecule.

A6. The nanopore device of any one of embodiments A1 to A5, further comprising a tether molecule in effective connection with the analyte binding molecule and the interior sidewall surface of the channel.

A7. The nanopore device of any one of embodiments A1 to A6, wherein the analyte binding molecule is an antibody or functional antibody fragment.

A8. The nanopore device of embodiment A6 or A7, wherein the tether molecule is in effective connection with the Fc region or hinge region of an antibody or functional antibody fragment.

A9. The nanopore device of any one of embodiments A6 to A8, wherein the tether molecule independently is chosen from a molecule comprising a silane, a thiol, phosphonic acid, amine, or carboxylic acid.

A10. The nanopore device of any one of embodiments A6 to A9, wherein the tether molecule is covalently attached to the interior sidewall surface of the channel.

A11. The nanopore device of any one of embodiments A6 to A10, wherein the analyte binding molecule is covalently attached to the tether molecule.

A12. The nanopore device of any one of embodiments A6 to A10, wherein the analyte binding molecule is non-covalently attached to the tether molecule.

A12.1. The nanopore device of any one of embodiments A6 to A12, wherein the analyte binding molecule is linked to the tether molecule or modifying molecule by a cross linking molecule.

A12.2. The nanopore device of embodiment A12.1, wherein the tether molecule or modifying molecule is directly attached to an interior sidewall surface of the channel.

A13. The nanopore device of any one of embodiments A1 to A12.2, wherein the minimum effective radius at the sensing zone in the channel is about 0.25 nanometers to about 500 nanometers.

A14. The nanopore device of any one of embodiments A1 to A13, wherein the analyte binding molecules are effectively attached to a zone on the interior sidewall surface of the channel.

A15. The nanopore device of embodiment A14, wherein the length of the zone is a portion of the length of the interior sidewall surface of the channel.

A16. The nanopore device of embodiment A15, wherein the zone extends around the circumference of the interior sidewall surface of the channel.

A17. The nanopore device of any one of embodiments A6 to A16, wherein the analyte binding molecule and tether molecule are configured to form a void within the interior of the channel.

A18. The nanopore device of embodiment A17, wherein the void is effectively defined by a plurality of analyte binding molecules and tether molecules and the effective center point of the void is substantially co-centric with the center point of the proximal opening.

A18.1. The nanopore device of embodiment A17 or A18, wherein the effective radius of the void is about 1 to 100 times the effective radius of an analyte that binds to one or more of the analyte binding molecules.

A19. The nanopore device of embodiment A17 or A18, wherein the effective radius of the void is about 1 to 2 times the effective radius of an analyte that binds to one or more of the analyte binding molecules.

A20. The nanopore device of any one of embodiments A17 to A19, wherein the effective radius of the void is determined by the equation $Radius_{sensing} = Radius_{channel} - (Length_{tether} + Length_{analyte\ binding\ molecule})$.

A21. The nanopore device of any one of embodiments A1 to A20, wherein a peptide, polypeptide, antigen, antibody or molecule analyte that can specifically bind to one or more of the analyte binding molecules is diagnostic for the presence, absence, amount or property of one or more pathogens, biomarkers, chemical contaminants, organic contaminants, drugs or combination thereof.

A22. The nanopore device of any one of embodiments A1 to A21, wherein the channel is cylindrical.

A23. The nanopore device of any one of embodiments A1 to A21, wherein the channel forms a frustrum A24. The nanopore device of any one of the embodiments of A1 to A23, wherein the first surface is coated with modifying molecules.

A25. The nanopore device of embodiment A24, wherein the modifying molecules prevent the analyte molecules from binding to the first surface of the nanopore device.

A26. The nanopore device of embodiment A24 or A25, wherein the modifying molecules are silane molecules.

A27. The nanopore device of embodiment A26, wherein the silane molecules are 3-cyanopropyldimethylchlorosilane.

B1. A method for detecting the presence, absence, amount or property of an analyte, comprising:
  (a) contacting a sample that may comprise an analyte with a nanopore device under conditions in which the analyte, if present in the sample, is captured in a sensing region of the device, which nanopore device comprises:
    a solid support that comprises a first surface, an opposing second surface, and a wall or walls between the first surface and the second surface;
    a channel in the solid support that comprises a proximal opening at the first surface, a distal opening at the second surface and an interior sidewall surface; and
    non-cyclic analyte binding molecules attached effectively by covalent linkage to the interior sidewall surface of the channel, each of which analyte binding molecules can specifically bind to an analyte; whereby the analyte binding molecules form the sensing region in the channel; and
  (b) measuring a property of the sensing region, whereby the presence, absence, amount or property of the analyte in the sample is determined by a change in the property measured in (b).

B2. The method of embodiment B1, wherein the property of the analyte is a kinetic parameter that characterizes the binding of the analyte to the analyte binding molecule.

B3. The method of embodiment B2, wherein the kinetic parameter is an off rate $k_{off}$.

B4. The method of embodiment B2, wherein the kinetic parameter is an on rate $k_{on}$.

B5. The method of embodiment B2, wherein the kinetic parameter is an affinity constant.

B6. The method of any one of embodiments B2 to B5, wherein the affinity constant is determined by $k_{on}$ and $k_{off}$.

B7. The method of any one of embodiments B2 to B6, wherein the kinetic parameter is determined by a change in fluorescence.

B8. The method of any one of embodiments B1 to B7, wherein the property of the sensing region measured is conductance.

B9. The method of embodiment B8, wherein the property of the sensing region measured is ion conductance.

B10. The method of embodiment B9, which comprises measuring a change in ion current rectification by a process comprising measuring the ion conductance at two or more voltages that are of equal magnitude and opposite voltage bias polarities.

B11. The method of embodiment B10, wherein the ion current rectification is measured at least once before analyte binding and at least once after analyte binding.

B12. The method of embodiment B10 or B11, wherein the voltage bias is from about −1000 to about 1000 mV.

B13. The method of any one of embodiments B1 to B12, wherein the property of the sensing region measured is a current blocking event.

B14. The method of embodiment B13, which comprises detecting the presence or absence of a reduction in the measured current resulting from the analyte binding to the analyte binding molecule.

B15. The method of any one of embodiments B1 to B14, which comprises releasing an analyte captured in the device.

B16. The method of embodiment B15, which comprises increasing the magnitude of the current, reversing the polarity of the current, reversing the polarity of the current and increasing the magnitude of the reversed current, applying pressure in a direction opposite to the capture direction, applying pressure in the direction to the capture direction, or a combination of the foregoing.

C1. A method of fabricating a nanopore device, comprising:
  (a) modifying at least a portion of an interior sidewall surface of a channel of a solid support with a first set of modifying molecules, which solid support comprises a first surface, an opposing second surface, and a wall or walls between the first surface and the second surface, and which channel comprises a proximal opening at the first surface, a distal opening at the second surface and the interior sidewall surface;
  (b) conjugating non-cyclic analyte binding molecules to the first set of modifying molecules, which analyte binding molecules can specifically bind to an analyte; whereby a nanopore device is fabricated.

C2. The method of embodiment C1, comprising, prior to (a), modifying the interior sidewall surface with a second set of modifying molecules and conjugating the first set of modifying molecules to the second set of modifying molecules.

C3. The method of embodiment C1 or C2, comprising, after (a) and before (b), determining the effective radius of a void in the channel, which void is defined by the first set of modifying molecules.

C4. The method of any one of embodiments C1 to C3, comprising, after (b), determining the effective radius of a void in the channel, which void is defined by the analyte binding molecules.

C5. The method of any one of embodiments C1 to C4, comprising blocking portions of the inner sidewall surface of the channel with a third set of modifying molecules that are not conjugated to the first set of modifying molecules or the second set of modifying molecules.

C6. The method of any one of embodiments C1 to C5, comprising prior to (a) modifying the first surface with a fourth set of modifying molecules.

C7. The method of embodiment C6, wherein the fourth set of modifying molecules prevent binding of the analyte binding molecule to the first surface.

C8. The method of any one of embodiments C1 to C7, which comprises inserting a wire into the channel of the solid support.

C9. The method of embodiment C8, which comprises modifying the first surface with the fourth set of modifying molecules that prevent binding of the analyte binding molecule to the first surface.

C10. The method of embodiment C9, which comprises etching the wire after the first surface is modified with the fourth set of modifying molecules, which etching reveals a portion of the interior sidewall surface of a channel.

C11. The method of embodiment C10, wherein the portion revealed by the etching is modified with the first set of modifying molecules.

C12. The method of embodiment C11, which comprises further etching or removing the wire, which etching or removing reveals another portion or the remainder of the interior surface of the channel.

C13. The method of embodiment C12, wherein the portion or remainder of the interior surface of the channel revealed by the further etching or removing is modified with the third set or the fourth set of modifying molecules.

C14. The method of embodiment C11, wherein the portion or remainder of the interior surface of the channel revealed by the further etching or removing is modified with a fifth set of modifying molecules that permit effective linkage of a second analyte binding molecule.

C15. The method of embodiment C14, wherein the second analyte binding molecule is non-cyclic.

C16. The method of embodiment C9, which comprises etching or removing the wire after the first surface is modified with the fourth set of modifying molecules, which etching reveals the interior sidewall surface of a channel.

C17. The method of embodiment C16, wherein the interior sidewall surface revealed by the etching or removing is modified with the first set of modifying molecules.

C18. The method of any one of embodiments C8 to C17, wherein the wire is a sharpened wire.

C19. The method of embodiment C18, wherein the tip of the sharpened wire comprises a cone or frustrum shape.

D1. The method of any one of embodiments B1 to B16 and C1 to C19, wherein the device comprises a plurality of analyte binding molecules that are identical to one another.

D2. The method of any one of embodiments B1 to B16 and C1 to C19, wherein the device comprises a plurality of analyte binding molecules that are a mixture of different analyte binding molecule species.

D3. The method of any one of embodiments B1 to B16, C1 to C19 and D1 or D2, wherein the analyte binding molecule independently is chosen from an antibody, antigen, ligand, lectin, aptamer, receptor or combination thereof.

D4. The method of any one of embodiments B1 to B16, C1 to C19 and D1-D3, wherein the analyte binding molecule specifically binds to an analyte chosen from a peptide, polypeptide, antibody, antigen, or molecule.

D5. The method of any one of embodiments B1 to B16, C1 to C19 and D1-D4, wherein the device further comprises a tether molecule or modifying molecule in effective connection with the analyte binding molecule and the interior sidewall surface of the channel.

D6. The method of any one of embodiments B1 to B16, C1 to C19 and D1-D5, wherein the analyte binding molecule is an antibody or functional antibody fragment.

D7. The method of any one of embodiments B1 to B16, C1 to C19 and D5 or D6, wherein the tether molecule or modifying molecule is in effective connection with the Fc region or hinge region of an antibody or functional antibody fragment.

D8. The method of any one of embodiments B1 to B16, C1 to C19 and D5-D7, wherein the tether molecule or modifying molecule independently is chosen from a molecule comprising a silane, a thiol, phosphonic acid, amine, or carboxylic acid.

D9. The method of any one of embodiments B1 to B16, C1 to C19 and D5-D9, wherein the tether molecule or modifying molecule is covalently attached to the interior sidewall surface of the channel.

D10. The method of any one of embodiments B1 to B16, C1 to C19 and D5-D10, wherein the analyte binding molecule is covalently attached to the tether molecule or modifying molecule.

D11. The method of any one of embodiments B1 to B16, C1 to C19 and D5-D10, wherein the analyte binding molecule is non-covalently attached to the tether molecule or modifying molecule.

D11.1. The method of any one of embodiments B1 to B16, C1 to C19 and D5-D11, wherein the analyte binding molecule is linked to the tether molecule or modifying molecule by a cross linking molecule.

D11.2. The method of embodiment D11.1, wherein the tether molecule or modifying molecule is directly attached to an interior sidewall surface of the channel.

D12. The method of any one of embodiments B1 to B16, C1 to C19 and D1-D11.2, wherein the effective radius of the sensing zone in the nanopore channel is about 0.25 nanometers to about 500 nanometers.

D13. The method of any one of embodiments B1 to B16, C1 to C19 and D1-D12, wherein the analyte binding molecules are effectively attached to a zone on the interior sidewall surface of the channel.

D14. The method of any one of embodiments B1 to B16, C1 to C19 and D13, wherein the length of the zone is a portion of the length of the interior sidewall surface of the channel.

D15. The method of any one of embodiments B1 to B16, C1 to C19 and D14, wherein the zone extends around the circumference of the interior sidewall surface of the channel.

D16. The method of any one of embodiments B1 to B16, C1 to C19 and D1-D15, wherein the analyte binding molecule and tether molecule or modifying molecule are configured to form a void within the interior of the channel.

D17. The method of any one of embodiments B1 to B16, C1 to C19 and D16, wherein the void is effectively defined by a plurality of analyte binding molecules and tether molecules or modifying molecules and the effective center point of the void is substantially co-centric with the center point of the proximal opening.

D17.1. The method of any one of embodiments B1 to B16, C1 to C19 and D16 or D17, wherein the effective radius of the void is about 1 to 100 times the effective radius of an analyte that binds to one or more of the analyte binding molecules.

D18. The method of any one of embodiments B1 to B16, C1 to C19 and D16 or D17 or D17.1, wherein the effective radius of the void is about 1 to 2 times the effective radius of an analyte that binds to one or more of the analyte detection molecules.

D19. The method of any one of embodiments B1 to B16, C1 to C19 and D16-D18, wherein the effective radius of the void is determined by the equation $Radius_{sensing} = Radius_{channel} - (Length_{tether} + Length_{analyte\ binding\ molecule})$.

D20. The method of any one of embodiments B1 to B16, C1 to C19 and D1-D19, wherein a peptide, polypeptide, antigen, antibody or molecule analyte that can specifically bind to one or more of the analyte binding molecules is diagnostic for the presence, absence or amount of one or more pathogens, biomarkers, chemical contaminants, organic contaminants, drugs or combination thereof.

D21. The method of any one of embodiments B1 to B16, C1 to C19 and D1-D20, wherein the channel is cylindrical.

D22. The method of any one of embodiments B1 to B16, C1 to C19 and D1-D20, wherein the channel forms a frustrum.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claims that follow.

What is claimed is:

1. A nanopore device, comprising:
a solid support that comprises a first surface, an opposing second surface, and a wall or walls between the first surface and the second surface;
a conical pore of nanometer dimensions in the solid support that comprises a proximal opening at the first surface, a distal opening at the second surface and an interior sidewall surface;
analyte binding molecules, that can specifically bind to an analyte, attached effectively by covalent linkage to a zone that is a portion of the length of the interior sidewall surface of the pore; whereby the analyte binding molecules form a sensing region in the pore; and the first surface and the interior sidewall surface that is not part of the zone, each comprising blocking molecules applied as a coating, wherein the blocking molecules are configured to prevent the analyte binding molecules from binding to the first surface and from binding to the interior sidewall surface that is not part of the zone.

2. The nanopore device of claim 1, wherein no cyclic molecules are linked or effectively linked to the nanopore device.

3. The nanopore device of claim 1, wherein the analyte binding molecule independently is chosen from an antibody, functional antibody fragment, antigen, ligand, lectin, aptamer, receptor or combination thereof.

4. The nanopore device of claim 1, comprising an attachment molecule in effective connection with the analyte binding molecule and the interior sidewall surface of the pore.

5. The nanopore device of claim 4, comprising a tether molecule in effective connection with the analyte binding molecule and the attachment molecule.

6. The nanopore device of claim 1, wherein the sensing region is a uniform and reproducible size.

7. The nanopore device of claim 1, wherein the zone extends around the circumference of the interior sidewall surface of the pore.

8. The nanopore device of claim 1, wherein the zone extends from a first depth from the proximal opening of the pore to a second depth from the proximal opening of the pore.

9. The nanopore device of claim 8, wherein the first depth is co-extensive with the first surface.

10. The nanopore device of claim 1, wherein the conical pore and the sensing region are configured to detect a kinetic parameter of the analyte.

11. The nanopore device of claim 1, wherein the conical pore and the sensing region are configured to detect a change in ion current rectification as a function of time.

12. A method for detecting the presence, absence, amount or property of an analyte, comprising:

contacting a sample that may comprise an analyte with a nanopore device of claim 1 under conditions in which the analyte, if present in the sample, is captured in a sensing region of the device; and, measuring a property of the sensing region, whereby the presence, absence, amount or property of the analyte in the sample is determined by a change in the property of the sensing region.

13. The method of claim 12, wherein the property of the analyte is a kinetic parameter.

14. The method of claim 13, wherein the kinetic parameter is the on rate or the off rate.

15. The method of claim 12, wherein the property of the sensing region measured is ion conductance.

16. The method of claim 15, which comprises measuring a change in ion current rectification by a process comprising measuring the ion conductance at two or more voltages that are of opposite voltage bias polarities.

17. The method of claim 16, wherein the change in ion current rectification is measured as a function of time.

18. A method of fabricating a nanopore device of claim 1, comprising:
(a) modifying at least a portion of an interior sidewall surface of a conical pore with a first set of modifying molecules; and
(b) conjugating analyte binding molecules to the first set of modifying molecules, which analyte binding molecules can specifically bind to an analyte;
whereby a nanopore device is fabricated.

19. The method of claim 18, which comprises modifying the first surface with a set of blocking molecules that prevent binding of the analyte binding molecule to the first surface.

20. The method of claim 18, comprising:
prior to (a) forming the pore in the solid support by sealing a wire into the solid support; and,
etching the wire after the first surface is modified with a set of blocking molecules that prevent binding of the analyte binding molecule to the first surface, which etching reveals a portion of the interior sidewall surface of a pore.

* * * * *